(12) United States Patent
Kelman et al.

(10) Patent No.: US 10,463,506 B2
(45) Date of Patent: Nov. 5, 2019

(54) ACETABULAR IMPLANT ALIGNMENT DEVICES AND METHODS

(71) Applicant: Smith & Nephew, Inc., Memphis, TN (US)

(72) Inventors: David C. Kelman, Somerville, TN (US); John Clausen, Germantown, TN (US); M. Scott Elliott, Memphis, TN (US); David L. Evans, Bartlett, TN (US); Kevin W. Belew, Hernando, MS (US); David W. Rister, Nesbit, MS (US); Phillip E. Frederick, Germantown, TN (US); Russell Walter, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 955 days.

(21) Appl. No.: 14/786,885

(22) PCT Filed: Apr. 25, 2014

(86) PCT No.: PCT/US2014/035535
§ 371 (c)(1),
(2) Date: Oct. 23, 2015

(87) PCT Pub. No.: WO2014/176548
PCT Pub. Date: Oct. 30, 2014

(65) Prior Publication Data
US 2016/0081819 A1 Mar. 24, 2016

Related U.S. Application Data

(60) Provisional application No. 61/944,932, filed on Feb. 26, 2014, provisional application No. 61/818,269, (Continued)

(51) Int. Cl.
*A61F 2/46* (2006.01)
*A61F 2/34* (2006.01)
(Continued)

(52) U.S. Cl.
CPC ........ *A61F 2/4609* (2013.01); *A61B 17/1746* (2013.01); *A61F 2/34* (2013.01);
(Continued)

(58) Field of Classification Search
CPC ........ A61F 2/4609; A61F 2/34; A61F 2/4684; A61B 17/1746
See application file for complete search history.

(56) References Cited

U.S. PATENT DOCUMENTS

2001/0053935 A1* 12/2001 Hartdegen ............ A61F 2/4014
623/19.12
2005/0065617 A1 3/2005 Barerra et al.
2011/0218642 A1 9/2011 Widmer

FOREIGN PATENT DOCUMENTS

CN 1373647 A 10/2002
CN 101257867 A 9/2008
(Continued)

OTHER PUBLICATIONS

European Office Action; European Patent Office; European Patent Application No. 14731433.0; dated Aug. 2, 2018; 3 pages.
(Continued)

*Primary Examiner* — Christian A Sevilla

(57) ABSTRACT

A trial medical instrument for aligning an acetabular component, comprising: a first portion configured to fit within a patient's acetabulum; and a second portion extending from the first portion; wherein the second portion extends from the first portion in a direction that mimics a shape formed by a femoral implant component coupled with an acetabular implant component when a femur to which the femoral
(Continued)

implant component is coupled is in a position relative to an acetabulum to which the acetabular implant component is coupled that is near an extent of a typical range of motion of the femur. As used herein, the phrase "extent of a typical range of motion" describes typical angular displacements of a femur as usually limited by patient anatomy.

30 Claims, 12 Drawing Sheets

Related U.S. Application Data filed on May 1, 2013, provisional application No. 61/816,415, filed on Apr. 26, 2013.

(51) Int. Cl.
  *A61B 17/17* (2006.01)
  *A61F 2/32* (2006.01)
  *A61F 2/30* (2006.01)

(52) U.S. Cl.
  CPC .............. *A61F 2/4684* (2013.01); *A61F 2/32* (2013.01); *A61F 2002/30604* (2013.01); *A61F 2002/30616* (2013.01); *A61F 2002/30617* (2013.01); *A61F 2002/4687* (2013.01)

(56) References Cited

FOREIGN PATENT DOCUMENTS

| CN | 101370437 A | 2/2009 |
| CN | 102014804 A | 4/2011 |
| EP | 0807426 A2 | 11/1997 |
| EP | 1634551 A2 | 3/2006 |
| JP | 2011-512926 A | 4/2011 |
| WO | 2009/106867 A1 | 9/2009 |
| WO | 2010046470 A1 | 4/2010 |

OTHER PUBLICATIONS

International Search Report; European Patent Office; International PCT Patent Application No. PCT/US2014/035535; dated Sep. 12, 2014; 2 pages.
Chinese Office Action and Search Report; Chinese Patent Office; Chinese Patent Application No. 201280043613.2; dated Oct. 11, 2016; 8 pages.
Australian Examination Report; Australian Patent Office; Australian Patent Application No. 2014256877; dated Mar. 22, 2018; 3 pages.
Japanese Notice of Reasons for Rejection; Japanese Patent Office; Japanese Patent Application No. 2016-510814; dated May 7, 2018; 13 pages.
European Office Action; European Patent Office; European Patent Application No. 14731433.0; dated Feb. 8, 2017; 4 pages.

* cited by examiner

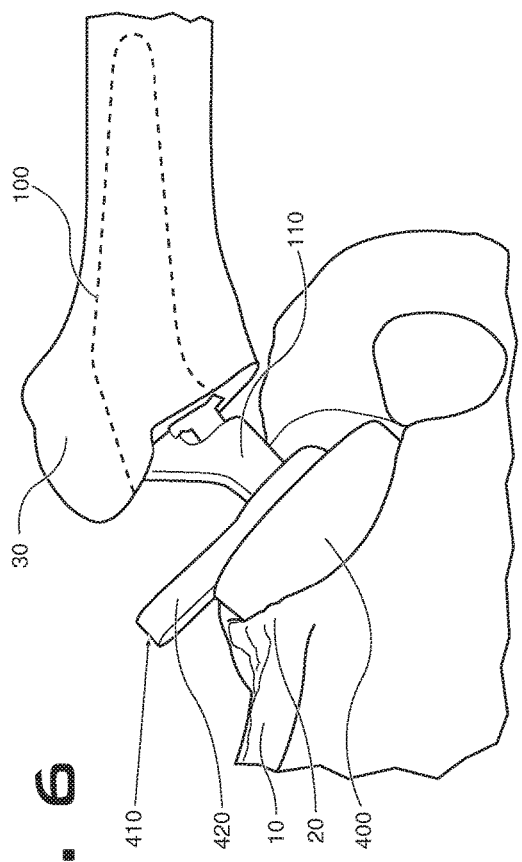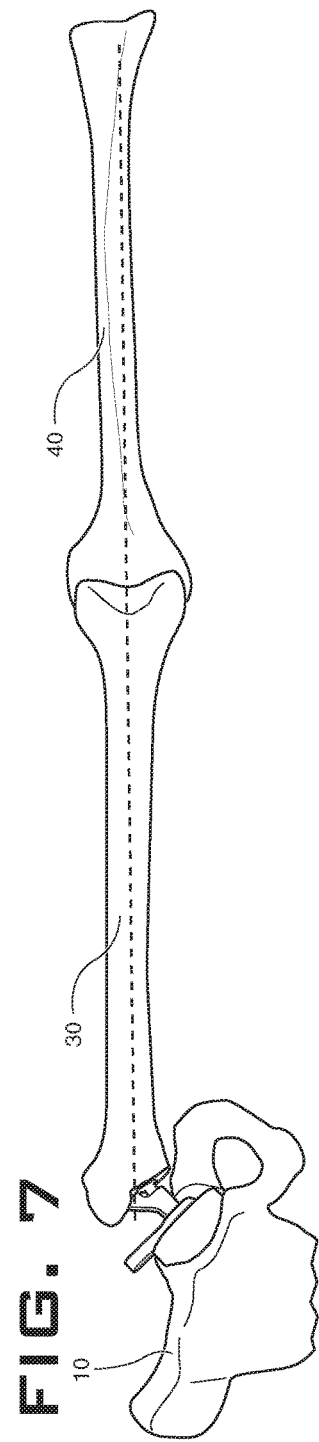
FIG. 6
FIG. 7

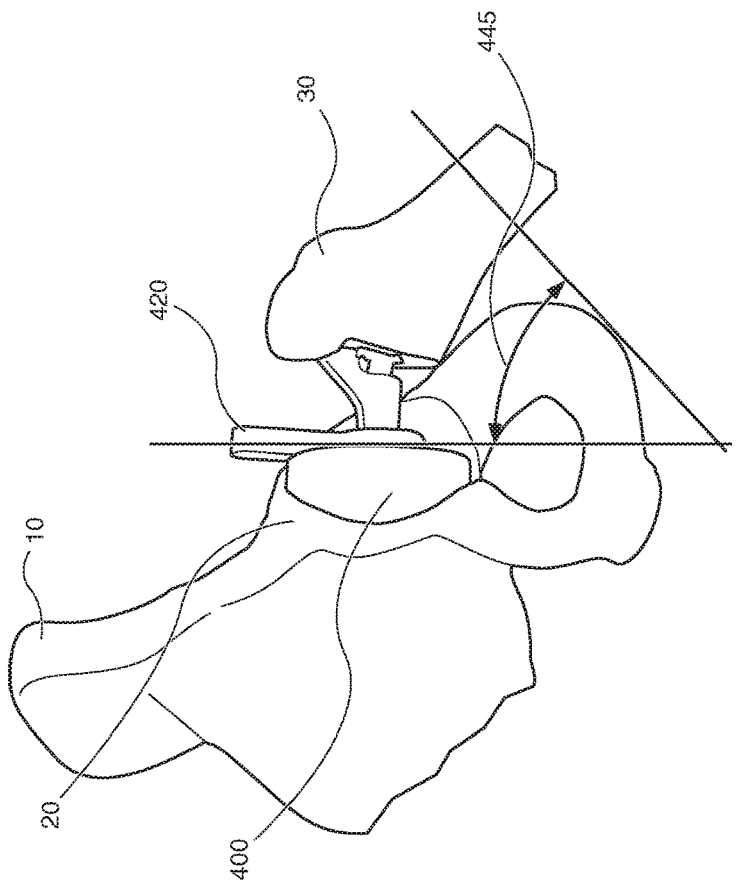
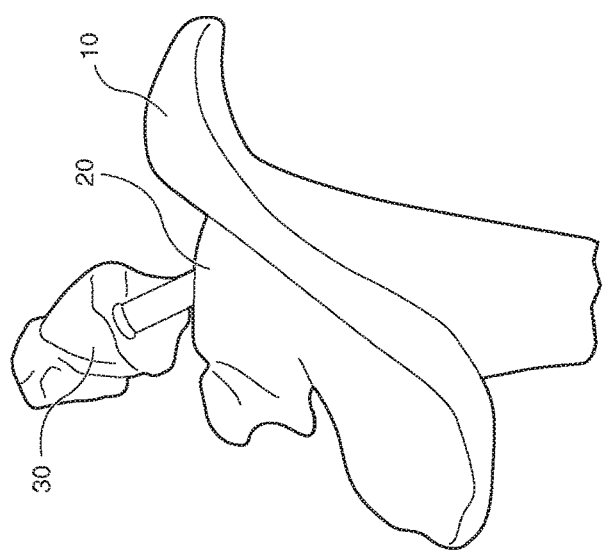

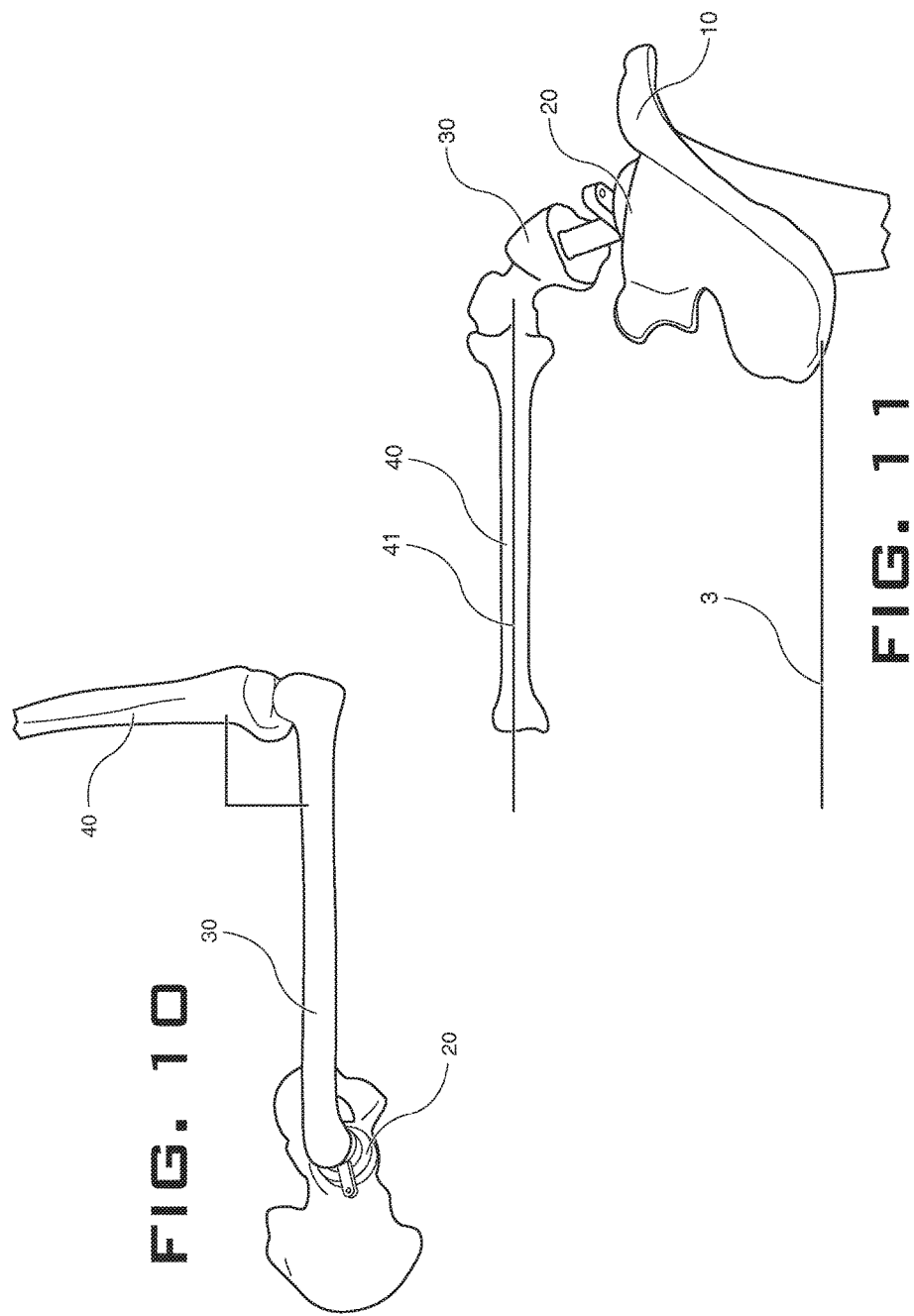

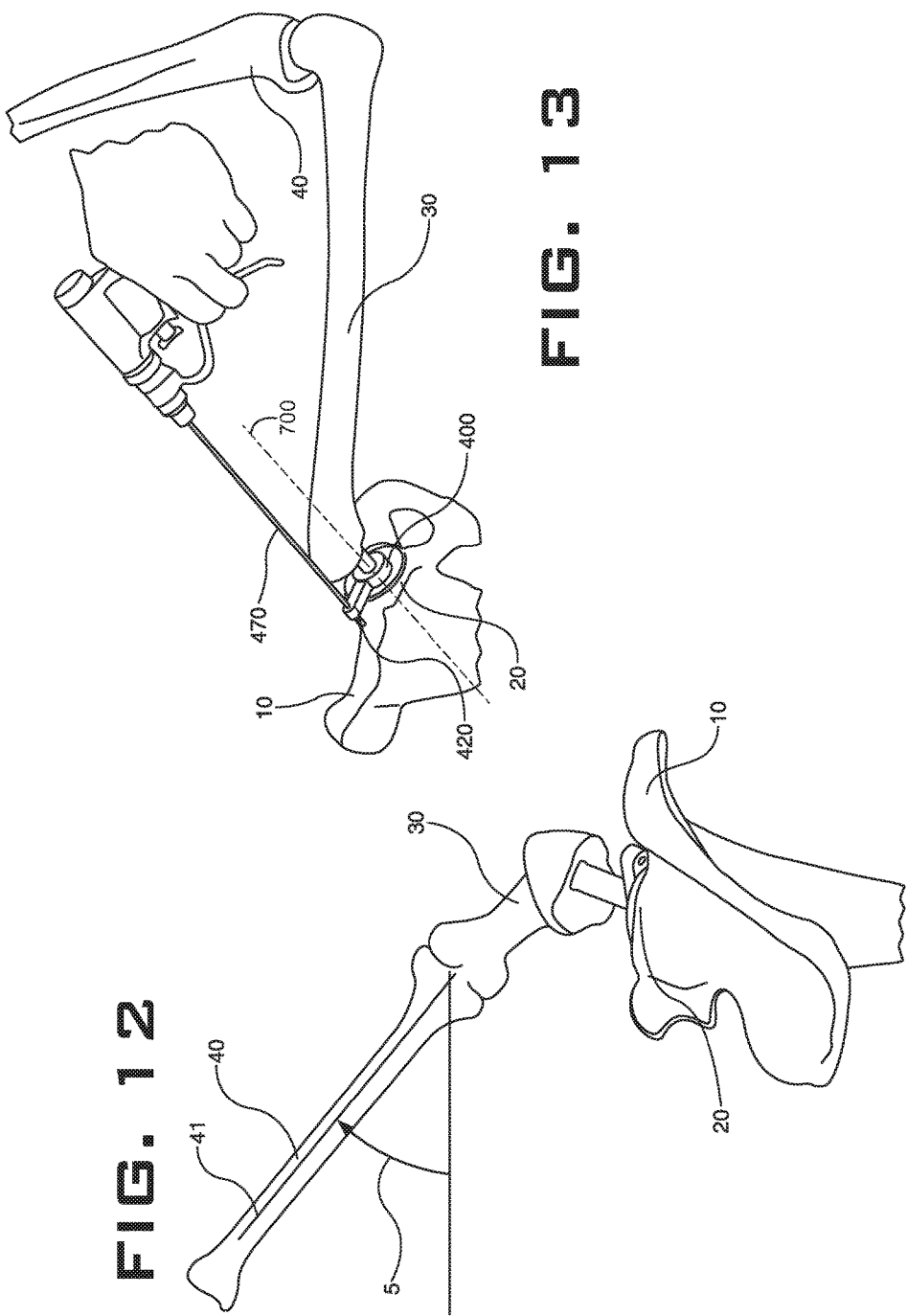

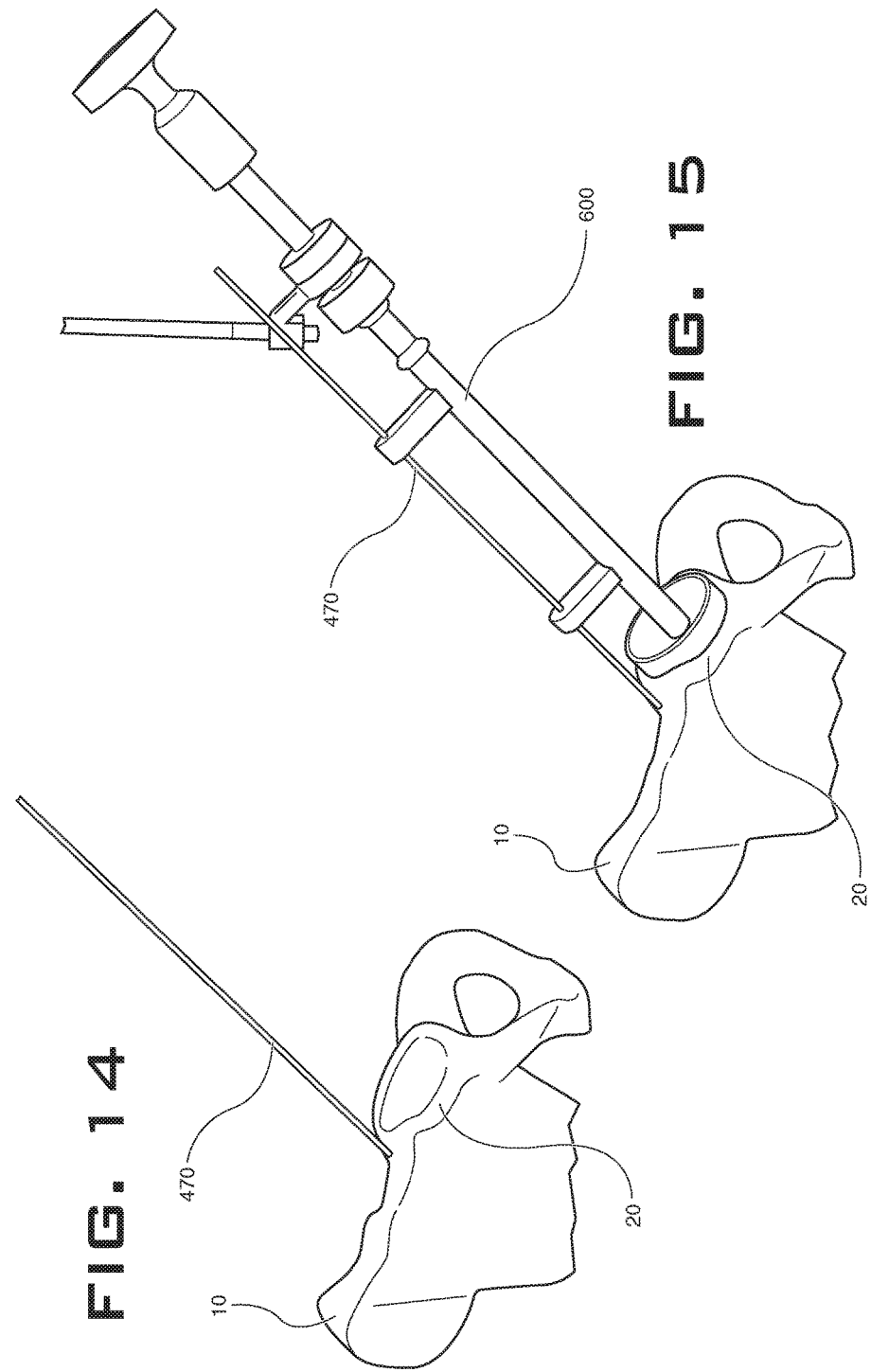

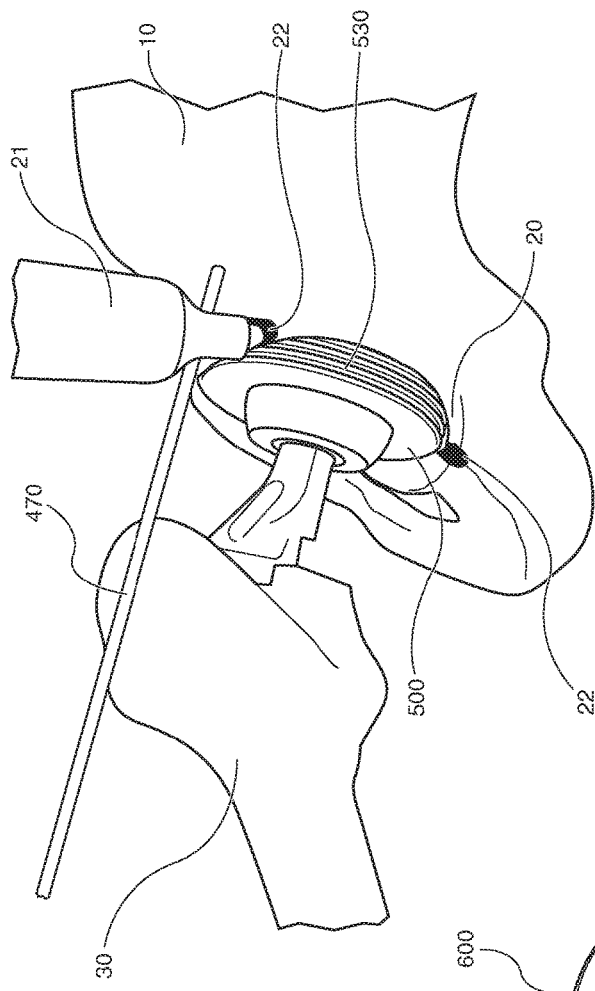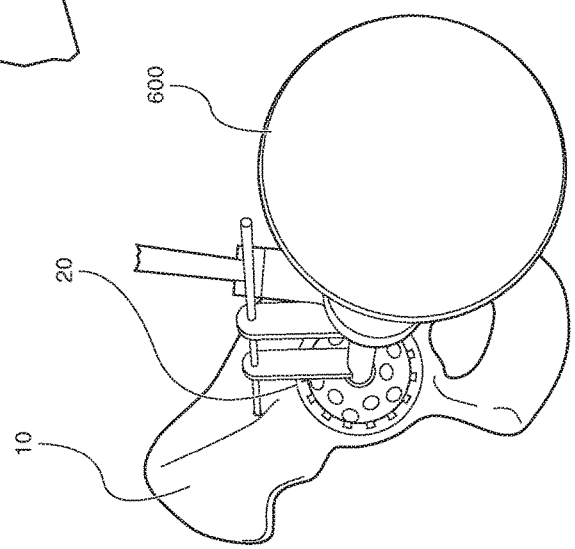

ACETABULAR IMPLANT ALIGNMENT DEVICES AND METHODS

CROSS-REFERENCE TO RELATED APPLICATIONS

This application is a United States National Phase filing of International Application No. PCT/US2014/035535, which claims the benefit of U.S. Provisional Patent Application No. 61/816,415, filed Apr. 26, 2013; U.S. Provisional Patent Application No. 61/818,269, filed May 1, 2013; and U.S. Provisional Patent Application No. 61/944,932, filed Feb. 26, 2014, each of which is hereby incorporated by reference herein in its entirety.

FIELD OF THE INVENTION

The present invention relates generally to the field of medical instruments, and more particularly relates to devices and methods for aligning acetabular components of hip arthroplasty systems for implantation in an acetabulum. Alignment may be accomplished by manipulation of a femur to which a specially configured medical instrument is coupled and further recording of the position of the medical instrument relative to the acetabulum.

BACKGROUND

The importance of alignment of acetabular components of hip arthroplasty systems is well-known in the field. Inaccurate alignment may lead to early and increased wear of components, loss of range of hip joint motion, patient pain, and hip joint dislocation. The most common means of acetabular component alignment currently in use utilize mechanical reference devices attached to acetabular trials or components during insertion. These reference devices are used to attempt to reference a patient's body axis and one or more planes within the patient's skeletal system. These methods have been practiced successfully, but anatomical variations, skeletal wear, and difficulties associated with maintaining visualization and reference to such anatomical references can lead to poor acetabular component alignment results. Computer-aided navigation systems have also been used to achieve alignment of acetabular components, but these systems also typically rely on anatomical references, which can lead to inconsistent alignment results. Improved systems may rely on one or both of designed and observed femoral range of motion relative to an acetabulum to guide the placement of acetabular components. Such systems may operate with less dependence on anatomical features of the acetabulum and surrounding skeletal structures to determine proper alignment of acetabular components.

SUMMARY

Disclosed herein are systems, devices and methods for aligning acetabular components of hip arthroplasty systems using a medical instrument coupled with a femur in a fixed and predetermined relationship. The medical instrument mimics the combined shape of a native femoral head, or implanted femoral head component, designed to move within an acetabular component that is later implanted into the patient. The orientation of the medical instrument corresponds to the orientation of the femoral head and the acetabular component when the femur is in a position near an extent of a typical range of motion of the femur. After the medical instrument is attached to the femur and placed within a patient's acetabulum, a surgeon moves and rotates the femur to position it near the extent of a typical range of motion or any other desired position. The medical instrument moves within the acetabulum while maintaining the fixed and predetermined relationship. Once the desired position of the femur is reached, the position of the medical instrument within the acetabulum is marked in one or more locations on the acetabulum. These marks provide guidance for reaming the acetabulum and/or implanting the acetabular component.

In one aspect, a method for aligning and implanting an acetabular component using a trial component includes coupling the trial component to a femur to align the trial component in a fixed, predetermined relationship with the femur, placing the trial component into an acetabulum such that the trial component can move within the acetabulum via the femur to indicate a position for implanting the acetabular component within the acetabulum, positioning the femur in a first position relative to the acetabulum, moving the femur from the first position to a second position relative to the acetabulum so that the fixed relationship between the trial component and the femur causes the trial component to move relative to the acetabulum, recording a position of the trial component relative to the acetabulum when the femur is in the second position, and implanting the acetabular component based on the recorded position of the trial component.

In certain implementations, recording a position of the trial component relative to the acetabulum includes marking the acetabulum. A surface of the trail component facing the acetabulum may include indicia, and marking the acetabulum includes marking locations on the acetabulum at which the indicia intersect edges of the acetabulum. A surface of the acetabular component facing the acetabulum includes additional indicia, and implanting the acetabular component based on the recorded position of the trial component further comprises aligning the additional indicia relative to the marked locations. In some implementations, marking the acetabulum includes marking locations at which a rim of the trial component intersects edges of the acetabulum.

In certain implementations, recording a position of the trial component relative to the acetabulum includes fixing a fastener into or near the acetabulum through a fastener guide formed in the trial component. The fastener may be fixed along an axis defined by a center of the acetabulum, or may be fixed at an angle offset from an axis defined by a center of the acetabulum. Implanting the acetabular component based on the recorded position of the trial component may include guiding the acetabular component along the fastener, and the method may include reaming the acetabulum after fixing a fastener into or near the acetabulum. Reaming the acetabulum may include guiding a reamer along the fastener.

In certain implementations, positioning the femur in a first position relative to the acetabulum includes positioning the femur in a neutral position. In certain implementations, moving the femur from the first position to the second position includes rotating the femur in anteversion. In certain implementations, the method includes flexing a knee at a distal end of the femur after positioning the femur in the first position.

According to one aspect, a trial medical instrument includes a first portion configured to fit within a patient's acetabulum and a second portion extending from the first portion. The second portion extends from the first portion in a direction that mimics a shape formed by a femoral implant component coupled with an acetabular implant component when a femur to which the femoral implant component is coupled is in a position relative to an acetabulum to which the acetabular implant component is coupled that is near an extent of a typical range of motion of the femur.

In certain implementations, the trial medical instrument includes indicia etched into a surface of the first portion that is configured to face the acetabulum, with the indicia providing a reference for alignment relative to the acetabulum. The indicia may include parallel lines and/or numerical or alphabetical characters.

In certain implementations, the trial medical instrument includes a fastener guide configured to direct a fastener along a trajectory into or near the acetabulum to mark a desired position of the acetabular component relative to the acetabulum. The fastener guide may direct the fastener along an axis defined by a center of the acetabulum, or may direct the fastener along an axis at an angle offset from an axis defined by the center of the acetabulum. In some embodiments, the trial medical instrument includes a femoral interface that is configured to couple the medical instrument to the femur and/or a body to couple the medical instrument to the femoral interface.

According to one aspect, a system for aligning and implanting an acetabular component includes means for aligning a medical instrument in a predetermined relationship with a femur, means for indicating a position of the medical instrument within an acetabulum to provide guidance for placing the acetabular component within the acetabulum, and means for orienting the means for indicating in a fixed relationship with the means for aligning. The fixed relationship is substantially the same as the relationship between the acetabular component and a femoral component where the femur that is configured to be coupled with the femoral component is in a position relative to the acetabulum that is near an extent of a typical range of motion of the femur.

In certain implementations, the system comprises means for providing a reference for alignment of the means for indicating relative to the acetabulum. The system also includes means for directing a fastener along a trajectory into or near the acetabulum to mark a desired position of the acetabular component relative to the acetabulum. The means for directing may include means for directing the fastener at an angle to an axis defined by a center of the acetabulum. The system includes means for coupling the medical instrument to the femur and/or means for coupling the medical instrument to the means for coupling the medical instrument to the femur.

According to one aspect, a method for aligning and implanting an acetabular component includes using a trial medical instrument as described above. According to one aspect, a method as described above uses a trial medical instrument as described above.

According to one aspect, a medical instrument for aligning an acetabular component based upon a position of a femur relative to an acetabulum includes a femoral interface configured to couple with the femur to align the medical instrument in a predetermined relationship with the femur, an acetabular interface configured to be moved within the acetabulum to indicate a position for placement of the acetabular component within the acetabulum, and a body coupled between the femoral interface and the acetabular interface. The body orients the acetabular interface in a fixed relationship with the femoral interface. The fixed relationship of the acetabular interface relative to the femoral interface is substantially the same as the relationship between the acetabular component and a femoral component where the femur that is configured to be coupled with the femoral component is in a position relative to the acetabulum that is near an extent of a typical range of motion of the femur.

In certain implementations, the femoral interface of the medical instrument includes an intramedullary component to couple with a medullary canal of the femur. In certain embodiments, the acetabular interface of the medical instrument is at least in part spherical, and may be hemispherical. The acetabular interface may include indicia that provide a reference for marking the acetabulum to receive an acetabular component and/or indicia that provide a reference for determining the size and orientation of the acetabular interface relative to the acetabulum. The acetabular interface of the medical instrument may be configured to be moved within a reamed acetabulum or configured to be moved within an unreamed acetabulum.

In certain implementations, the femoral interface, the acetabular interface, and the body are a single piece. In other implementations, the acetabular interface and the body are a single piece and the femoral interface is configured to removably affix to the body. In yet other implementations, the femoral interface and the body are a single piece and the acetabular interface is configured to removably affix to the body.

In some implementations, the femur coupled to the medical instrument is in the position relative to the acetabulum that is near the extent of a typical range of motion of the femur in the predetermined position, and the position of the acetabular component in the acetabulum is a desired position. The desired position of the acetabular component may be a position where a plane of a rim of the acetabular component is substantially parallel with a periphery of the acetabulum. When the femur is in a position relative to the acetabulum that is near the extent of a typical range of motion of the femur, the femur may be moved from a generally neutral position to a rotated position by rotating the femur in a range of about 15-30 degrees of anteversion, and may be moved from a generally neutral position to a rotated position by rotating the femur by about 25 degrees of anteversion. The medical instrument includes a fastener guide configured to direct a bone fastener along a trajectory into bone to establish and maintain a relative position for an acetabular component relative to the bone.

Another embodiment is a medical instrument of a fixed, non-articulating shape that mimics the combined shape of a femoral hip replacement component designed to articulate with an acetabular hip replacement component. The shape that is mimicked may be the combined shape of the femoral hip replacement component and the acetabular hip replacement component when a femur that is configured to be coupled with the femoral component is in a position relative to the acetabulum that is near an extent of a typical range of motion of the femur. In some embodiments, when the femur coupled to the medical instrument is in the position relative to the acetabulum that is near the extent of a typical range of motion of the femur, the position of the acetabular component in the acetabulum is a desired position. The desired position of the medical instrument in the acetabulum is a position where a plane of a rim of an acetabular component of the medical instrument is substantially parallel with a periphery of the acetabulum.

In some implementations, when the femur is in a position relative to the acetabulum that is near the extent of a typical range of motion of the femur, the femur has been moved from a generally neutral position to a rotated position by rotating the femur in a range of about 15-30 degrees of anteversion. As an example, when the femur is in a position relative to the acetabulum that is near the extent of a typical range of motion of the femur, the femur has been moved from a generally neutral position to a rotated position by rotating the femur by about 25 degrees of anteversion.

Also discloses herein is a method of aligning an acetabular component based on a position of a femur relative to an acetabulum. The method may include providing a medical instrument for aligning the acetabular component that has a femoral interface configured to couple with the femur to align the medical instrument in a predetermined relationship with the femur, an acetabular interface configured to be moved within the acetabulum to indicate a position for placement of the acetabular component within the acetabulum, and a body coupled between the femoral interface and the acetabular interface, wherein the body orients the acetabular interface in a fixed relationship with the femoral interface. The method may also include coupling the medical instrument to the femur to align the medical instrument in a predetermined relationship with the femur, positioning the femur in a first position relative to the acetabulum, moving the femur to a second position relative to the acetabulum, recording the position of the acetabular interface relative to the acetabulum, and implanting the acetabular component based on the recorded position of the acetabular interface relative to the acetabulum.

According to one aspect, the method may include positioning the femur in a substantially neutral position. In some embodiments, moving the femur to a second position may include rotating the femur in anteversion. As an example, rotating the femur in anteversion includes rotating the femur in a range of about 15-30 degrees. In some implementations, rotating the femur in anteversion includes rotating the femur about 25 degrees.

In some embodiments, the method includes flexing a knee at the distal end of the femur after the act of positioning the femur in the first position. For example, the knee may be flexed in the range of about 60-120 degrees. The method includes marking the acetabulum. In some implementations, implanting the acetabular component based on the recorded position of the acetabular interface in the acetabulum may be guided by visualizing one or more marks on the acetabulum.

In some embodiments, the method includes fixing a fastener through a fastener guide on the medical instrument to bone in or near the acetabulum. In some implementations, implanting the acetabular component based on the recorded position of the acetabular interface in the acetabulum is guided by referencing the fastener in or near the acetabulum.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. The foregoing and other objects and advantages will be apparent upon consideration of the following detailed description, taken in conjunction with the drawings, in which like reference characters refer to like parts throughout, and in which:

FIG. 6 illustrates a front view of a leg in neutral extension with a medical instrument having one drill guide attached.

FIG. 7 illustrates a front view of a leg, including a tibia and a femur, in neutral extension with the medical instrument of FIG. 6 attached.

FIG. 8 illustrates a top view of a leg, including a tibia and a femur, in neutral extension with the medical instrument of FIG. 6 attached;

FIG. 9 illustrates a front view of a leg in neutral extension with the medical instrument of FIG. 6 attached;

FIG. 10 illustrates a lateral view of a leg, including a tibia and a femur with the knee in about 90 degrees of flexion, and with the medical instrument of FIG. 6 attached;

FIG. 11 illustrates a superior view of the illustration of FIG. 10;

FIG. 12 illustrates a superior view of the illustration of FIG. 10 in femoral internal rotation or anteversion;

FIG. 13 illustrates a front view of the illustration of FIG. 12 with a fastener attached to the pelvis;

FIG. 14 illustrates a front view of the pelvis and fastener of FIG. 13 with the medical instrument of FIG. 6 removed;

FIG. 15 illustrates a front view of the pelvis and fastener of FIG. 13 with a reamer being guided by the fastener;

FIG. 16 illustrates a lateral view of the pelvis and reamer of FIG. 15;

FIG. 17 illustrates a superior/anterior view of a pelvis with an attached fastener, a femur, and alternative medical instrument.

DETAILED DESCRIPTION

Figure 1:
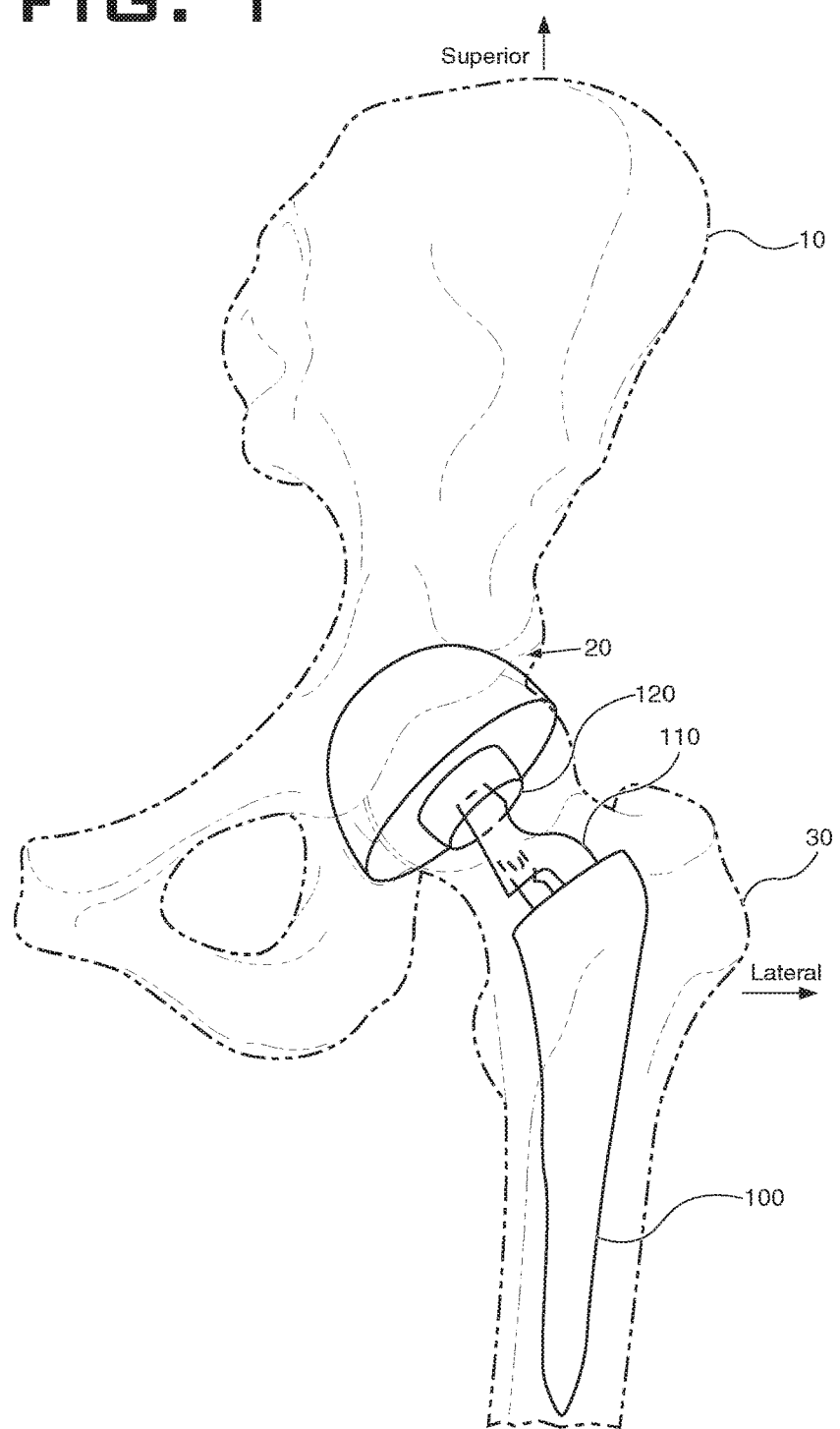
FIG. 1 illustrates a front view of a leg in neutral extension to which a medical instrument is attached.

To provide an overall understanding of the systems, devices, and methods described herein, certain illustrative embodiments will be described. Although the embodiments and features described herein relate to acetabular systems, it will be understood that components, adjustable systems, manufacturing methods, and other features outlined below may be combined with one another in any suitable manner and may be adapted and applied to medical devices and implants to be used in other surgical procedures, including, but not limited to, knee arthroplasty, shoulder arthroplasty, as well as foot, ankle, hand, and other extremity procedures. The following description of the depicted embodiments is merely exemplary in nature and is in no way intended to limit the invention, its application, or uses.

The embodiments herein utilize techniques that a surgeon may use pre-operatively, intra-operatively, and post-operatively to assess a patient's range of motion to provide guidance for proper alignment, placement and implantation of acetabular components, such as acetabular shells or other acetabular components, without having to rely on pre-determined anatomical landmarks or having to determine anatomical planes. Such techniques include, but are not limited to, total hip arthroplasty ("THA") to prospectively determine and define one or more of the orientation of the final acetabular implant, the femoral offset, and the leg length by means of mechanical, electrical or electro-mechanical trial instrumentation with and without the influence or guidance of natural anatomy. The data obtained through these techniques may then be used to guide and/or verify the final implant placement for a best-fit of standard hip arthroplasty system components in order to best restore natural biomechanics.

The mechanical methods to identify the optimal orientation for the acetabular component based upon the femoral head mapping is similar to that highlighted in U.S. Pat. No. 8,491,664, entitled, "System of Orienting Femoral Head for Acetabular Prosthesis Alignment," which is herein incorporated by reference in its entirety, with the exception that the native acetabulum is marked or recorded for proper orientation before or after reaming the acetabulum but prior to the component placement. In other embodiments, in addition to marking the acetabulum, the trial head may be marked or the trial head may be used as an indicator for the relative position of the component or shell in the acetabulum.

In some embodiments of the invention, a surgeon may determine anteversion and inclination angles by placing a medical instrument coupled to a femur into a native or reamed acetabulum and moving the femur to various positions, such as neutral and combined internal rotation and flexion. Then, based on indicia on the medical instrument, the surgeon may mark the acetabulum at some locations, so that the marks provide guidance for the placement of an acetabular component relative to the marks. The acetabular component may have markings on the surface facing the acetabulum to assist in placement relative to the marks on the acetabulum.

The medical instrument may include a unipolar head of a size that mimics the combined shape of a femoral head and an acetabular component ("CSFHAC") with orientations that typically would correspond to the neutral position of the femur and combined internal rotation and flexion. Embodiments of CSFHACs may be referred to herein at least in part as acetabular interfaces, acetabular trial components, or simply trial components. In some embodiments, CSFHACs may include both acetabular interfaces and portions of bodies coupled between the acetabular interfaces and femoral interfaces. There may be a plurality of CSFHACs in different sizes, and the size closest to the natural acetabulum may be selected in some embodiments. Similar techniques and devices may be used with a THA or a resurfacing procedure. A CSFHAC may be placed into the acetabulum after removal of the native femoral head and neck. The acetabulum may be in its basic state (unreamed) or may be reamed in various embodiments.

In some method embodiments, the CSFHAC is located in the patient's acetabulum and the leg is extended into a neutral position. The CSFHAC may be oriented into the corresponding neutral position, and the acetabulum marked. As examples, the mark may be made with a marking pen or cauterizer. The leg may be repositioned into the internal rotation and flexed positions. The CSFHAC may be placed into the corresponding position and the acetabulum marked. In some embodiments, the acetabulum is marked around the rim in a plurality of locations. If necessary, measures may also be taken from a bony landmark to corresponding indicia on the CSFHAC to ensure proper location of the acetabular component. The hip may be dislocated and the CSFHAC removed. If necessary, the acetabulum may be prepared for placement of the acetabular component if it has not already been prepared. The acetabular component may be placed on the inserter in a typical fashion. The acetabular component may be introduced into the acetabulum and orientated relative to the marks that have been transferred to the acetabulum; these marks provide a reference for the acetabular component for anteversion and inclination. If a measurement was made from a bony reference point, it may also aid in proper placement of the acetabular component. After insertion of the acetabular component relative to the marks and possibly other measurements, a traditional range of motion test may be completed to verify component position. Once verified, the acetabular component or implant may be impacted. In some embodiments, the acetabular component may have indicia that a similar to the indicia on the CSFHAC to assist in the orientation of the acetabular component relative to the marks on the bone. In some embodiments, a CSFHAC may have indicia on it to estimate the amount of uncovered area in the preferred orientation and be used to estimate the final uncovered area and orientation of the acetabular component. The indicia on the acetabular component may have marks on it corresponding to the CSFHAC that assist in reproducing the preferred uncovered areas. Note that the terms "position," "orientation," and "location" used throughout may each be used to designate three-dimensional placement and rotational state.

Figure 2:
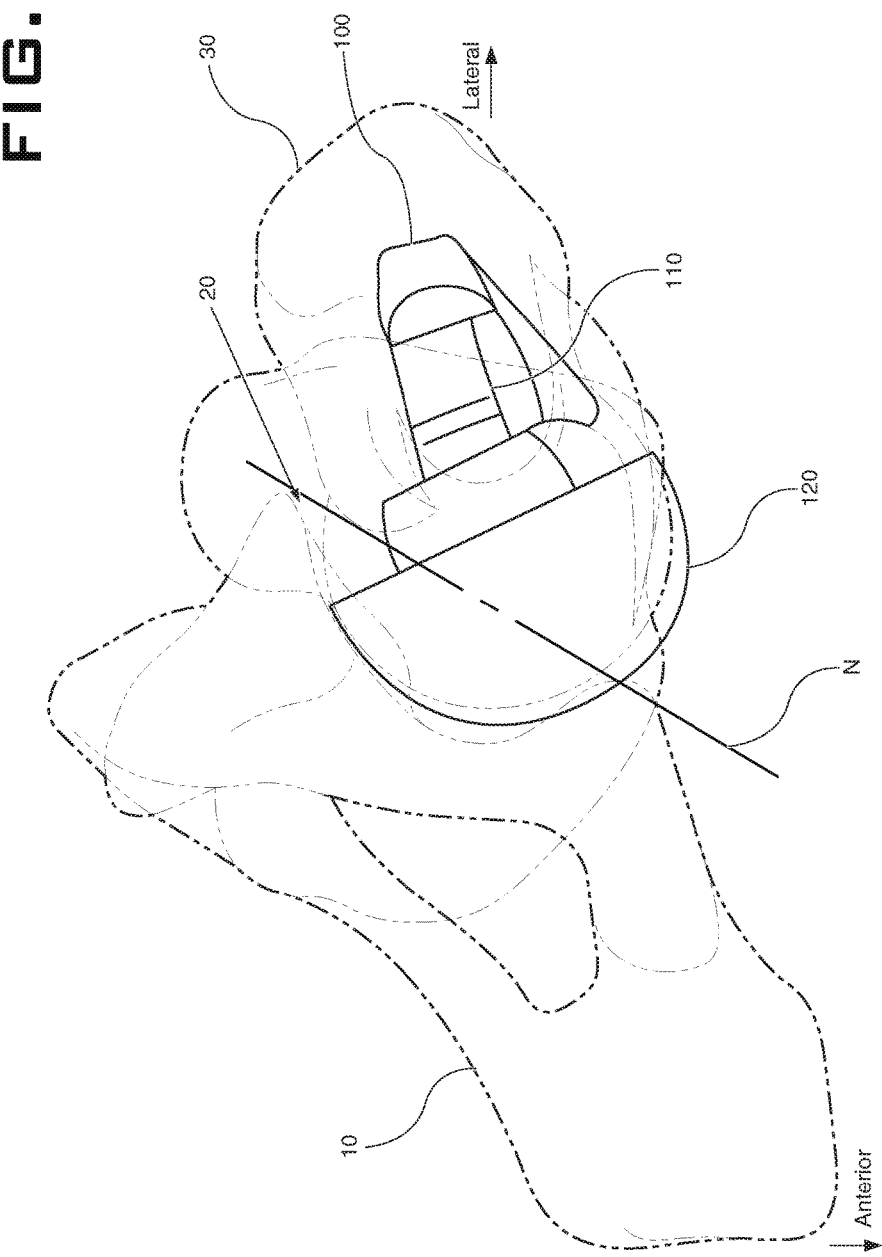
FIG. 2 illustrates a sectional superior view of the leg in neutral extension with the medical instrument of FIG. 1 attached.

FIGS. 1 and 2 illustrate a left hip 10 with an acetabulum 20. FIG. 2 illustrates a sectional top view of the femur 30 shown in FIG. 1. Although a left hip is illustrated, the invention is applicable to both left and right hips. FIGS. 1 and 2 also illustrate a femur 30 in neutral extension. In the depicted embodiment, a broach 100 has been placed into an intramedullary canal of the femur 30 and serves as a femoral interface configured to couple with the femur 30 to align in a predetermined relationship with the femur 30. Although the femoral interface depicted is an intramedullary component, in other embodiments, a femoral interface may connect to a femur by any other effective way, including by extramedullary mechanisms.

A CSFHAC 120 of the illustrated embodiment serves as an acetabular interface configured to be moved within the acetabulum to indicate a position for placement of an acetabular component of a hip arthroplasty system. The CSFHAC 120 illustrated is at least in part spherical, and more specifically, hemispherical. Other embodiments of an acetabular interface may have larger or smaller spherical portions, may not include spherical portions, and may be any effective combination of shapes. The CSFHAC 120 is designed so that where the leg is manipulated into certain positions (e.g., flexed and internally rotated, in anteversion), the plane of the CSFHAC 120 corresponds to the optimal acetabular component or shell placement for combined anteversion. The axis N (FIG. 2) represents the approximate natural version of the acetabulum 20. The illustrated CSFHAC 120 shown is configured by its size and shape to be moved within an unreamed acetabulum, the acetabulum 20. In other embodiments, a CSFHAC or another acetabular interface may be configured to be moved within a reamed acetabulum.

A trial neck 110 is used to connect the CSFHAC 120 to the broach 100, and thereby serves as a body coupled between the femoral interface and the acetabular interface to orient the acetabular interface in a fixed relationship with the femoral interface. In the illustrated embodiment, the broach 100, the trial neck 110, and the CSFHAC 120 are separate pieces, each being configured to be removable from the other in the order shown. In other embodiments, these or other configurations of a femoral interface, a body, and an acetabular interface may be other combinations of pieces or all a single piece. For example, an acetabular interface and a body may be a single piece and the femoral interface may be configured to removably affix to the body. By way of further example, a femoral interface and a body may be a single piece and an acetabular interface may be configured to removably affix to the body.

Figure 3:
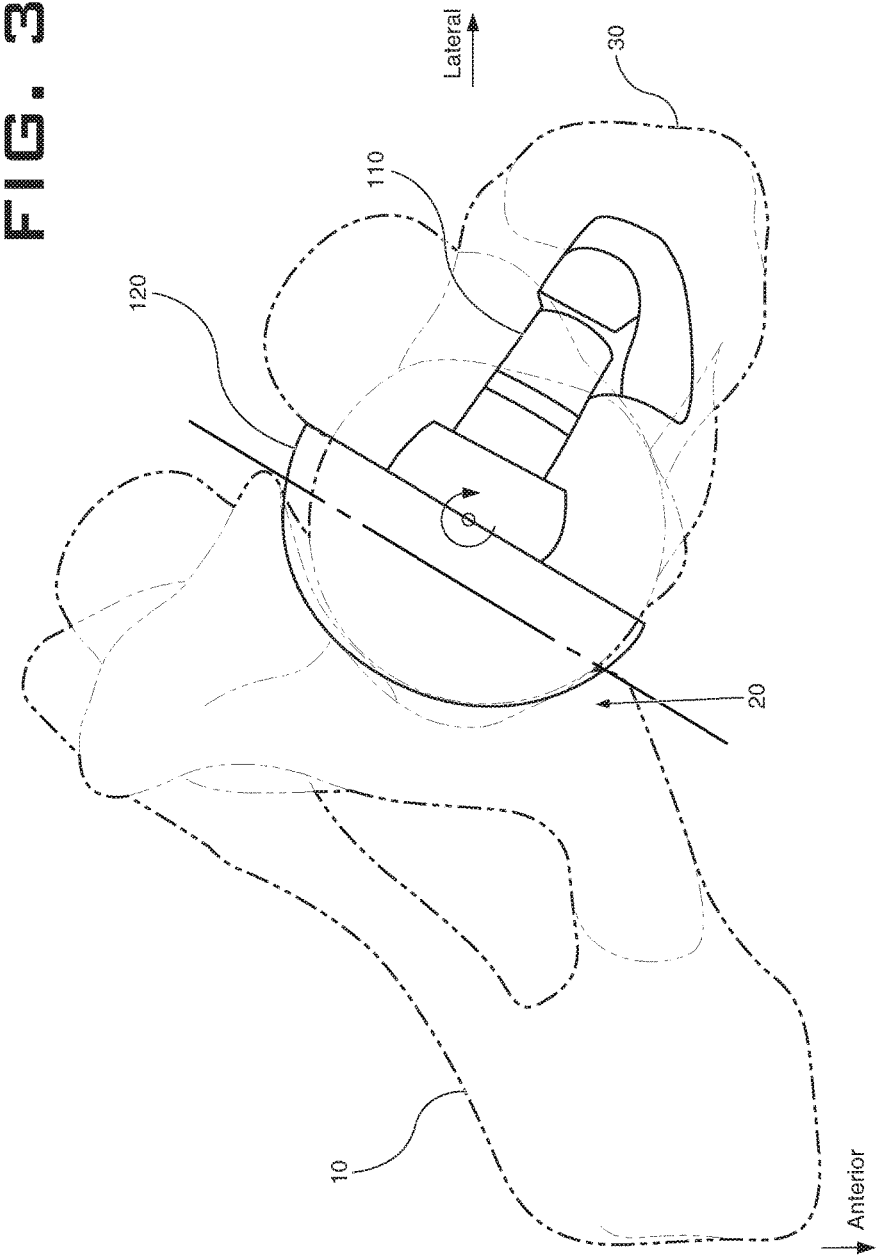
FIG. 3 illustrates a sectional superior view of the leg in femoral internal rotation or anteversion with the medical instrument of FIG. 1 attached.

FIG. 3 illustrates a sectional top view of the femur 30 of FIG. 2 in a flexed and internally rotated position (i.e., in anteversion). This places the CSFHAC 120 in the position depicted in FIG. 3, which in some embodiments corresponds with an optimal acetabular shell or other acetabular component placement for combined anteversion. Stated another way, the fixed relationship of the acetabular interface embodied in the CSFHAC 120 relative to the femoral interface embodied in the broach 100 is substantially the same as the relationship between a hip arthroplasty acetabular component and a hip arthroplasty femoral component where, when the acetabular component is implanted within the acetabulum and the femur 30 that is configured to be coupled to the hip arthroplasty femoral component is in a position relative to the acetabulum 20 that is near an extent of a typical range of motion of the femur 30, such as combined anteversion.

As used herein, the phrase "extent of a typical range of motion" describes typical angular displacements of a femur as usually limited by patient anatomy. Such extents may or may not describe angulation beyond which a dislocation or other injury would typically occur. As illustrated in FIG. 3, the medical instrument constructed of the broach 100, the trial neck 110, and the CSFHAC 120 is in a desired or optimal position relative to the acetabulum 20 after the femur 30 was moved to combined anteversion, which is near an extent of a typical range of motion of the femur 30. In the illustrated embodiment, the desired position of an acetabular component, as demonstrated by the acetabular interface, is a position where a plane of a rim of the acetabular interface or corresponding acetabular component is substantially parallel with a periphery of the acetabulum 20, as illustrated in FIG. 3. As used herein the term "periphery of the acetabulum" means a substantial average of irregular surfaces, understanding that surfaces of bone are typically geometrically irregular. In other embodiments, the desired position may correlate with positions best located to avoid the possibility of dislocations or that provide for optimal range of motion. By designing the medical instrument with an understanding of extents of typical ranges of motion required for proper function of hip arthroplasty devices, applying the medical instrument to a femur, and moving the femur to the corresponding extent of its range of motion, an acceptable alignment for an acetabular component can be recorded and then achieved. In some embodiments where a femur is in a position relative to an acetabulum that is near the extent of a typical range of motion of the femur, the femur has been moved from a generally neutral position to a rotated position by rotating the femur in a range of about 15-30 degrees of anteversion.

More specifically, in some embodiments where a femur is in a position relative to an acetabulum that is near the extent of a typical range of motion of the femur, the femur has been moved from a generally neutral position to a rotated position by rotating the femur by about 25 degrees of anteversion. Other embodiments may include different rotations, and where a different extent of a range of motion is used, a femur may be rotated in different directions and to other degrees of rotation.

Such a device may also be a medical instrument of a fixed, non-articulating shape that mimics the combined shape of a femoral hip replacement component designed to articulate with an acetabular hip replacement component. An example of such a medical instrument is the combination of the broach 100, the trial neck 110, and the CSFHAC 120 when fixed together. The shape that is mimicked may be the combined shape of the femoral hip replacement component and the acetabular hip replacement component implanted in the acetabulum, when a femur that is configured to be coupled with the femoral component is in a position relative to the acetabulum that is near an extent of a typical range of motion of the femur.

Figure 4:
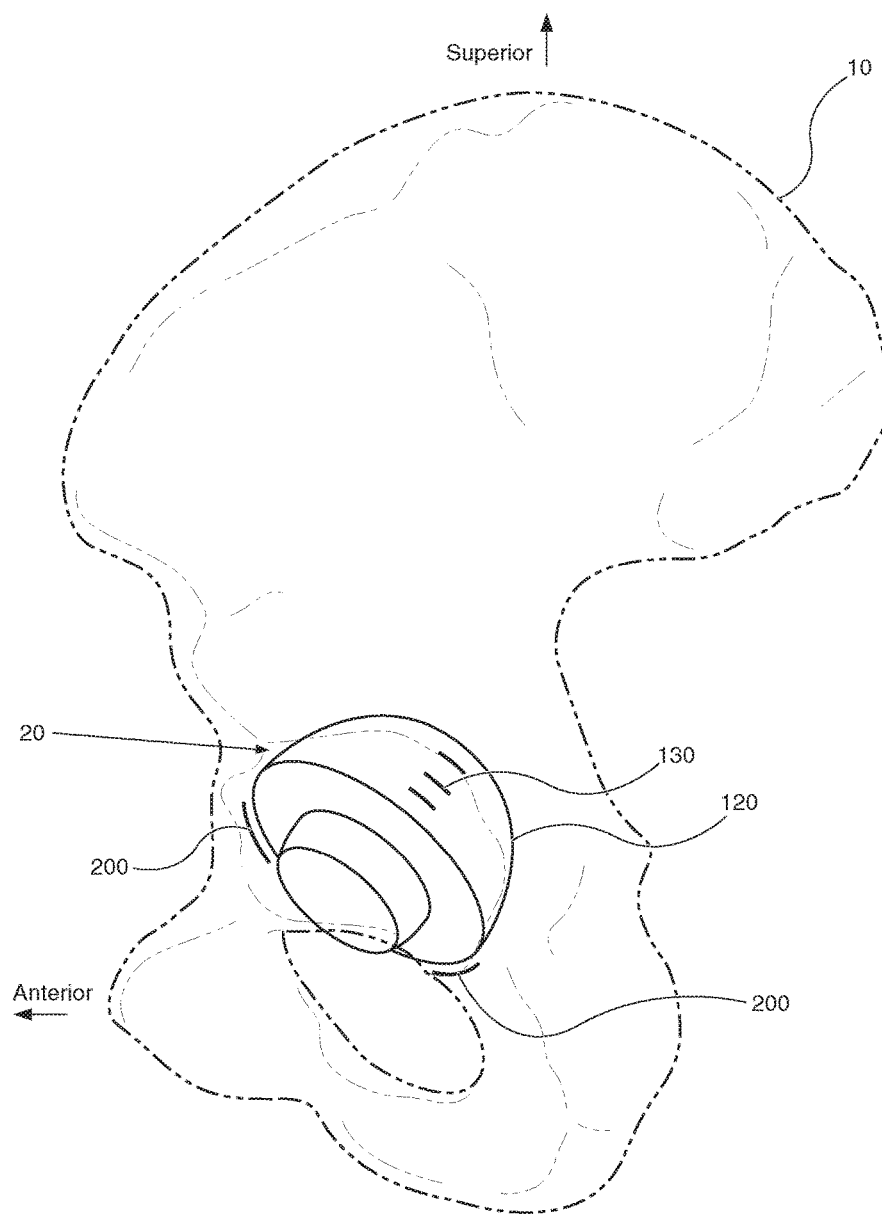
FIG. 4 illustrates an isometric view of the acetabulum with a portion of the medical instrument of FIG. 1 attached.

While the CSFHAC 120 is in the illustrated position of FIGS. 3 and 4, the acetabulum may be marked with one or more markings 200 (FIG. 4). The markings 200 may be used for guiding a reamer and/or for placement of the acetabular shell or component. FIG. 4 illustrates a lateral view of the acetabulum 20 with the CSFHAC 120 and the markings 200. In the depicted embodiment, the markings 200 are made near a leading edge of the acetabulum 20 and a posterior edge of the acetabulum 20. In some embodiments, the CSFHAC 120 may include indicia 130 configured to assist in aligning and marking a position of the CSFHAC and in guiding the eventual placement of an acetabular component. The indicia may be etched into a surface of the CSFHAC, may be painted on a surface of the CSFHAC, or may outwardly extend from a surface of the CSFHAC. Although any surface of the CSFHAC may be used, in a preferred embodiment the indicia are located on a surface of the CSFHAC that faces the acetabulum. As an example, the indicia 130 may be parallel and spaced apart to provide a reference to assist with alignment of the acetabular shell or component, for example with lines, grooves or ridges. In another example, indicia may include alphabetical characters or numeral characters etched into a surface, painted on a surface, or protruding from a surface. In some embodiments, there may be provided an acetabular shell or component with corresponding indicia. The indicia on the acetabular shell or component may be aligned relative to the marks 200 on the acetabulum. In an alternative embodiment, there is provided a kit of CSFHACs of different sizes and orientations with corresponding acetabular shells or components. In the kit, the CSFHACs and the acetabular shells or components may have corresponding indicia.

Figure 5:
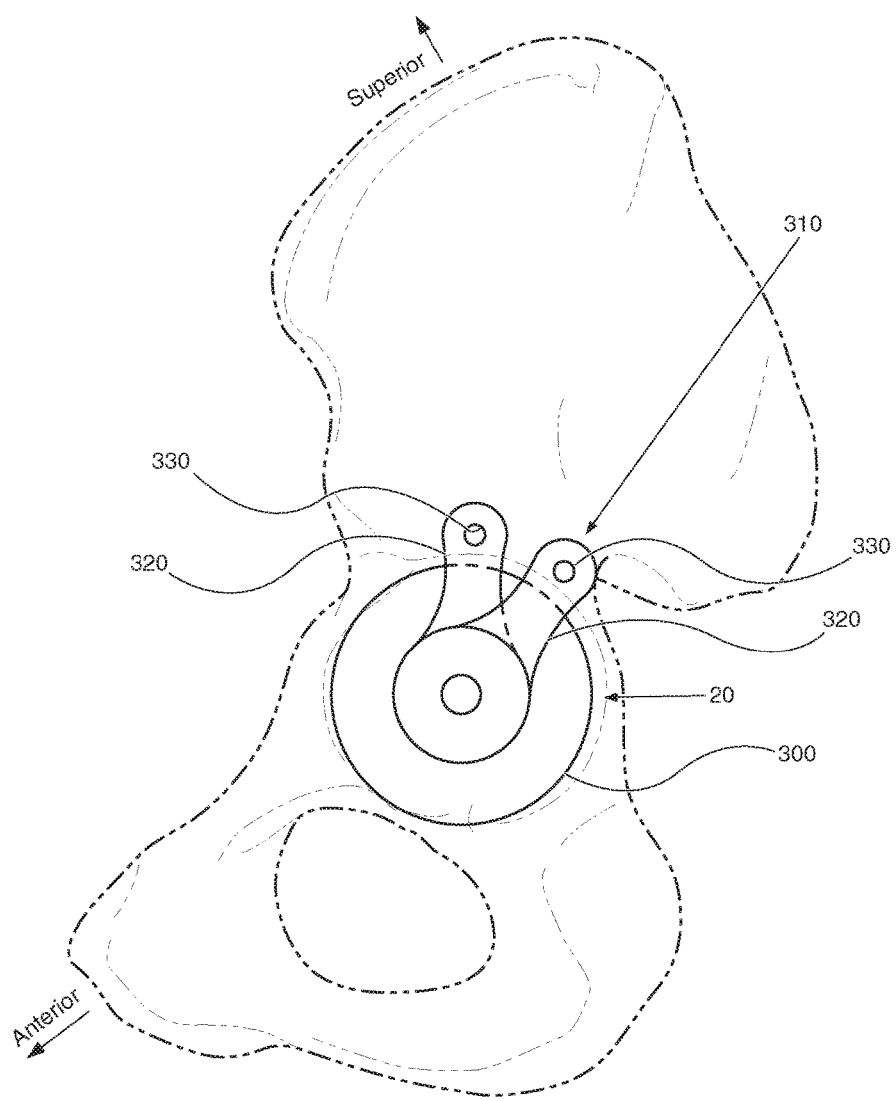
FIG. 5 illustrates a lateral view of the acetabulum with a portion of a medical instrument attached.

In some embodiments, a medical instrument including one or more of a femoral interface, an acetabular interface, and a body may incorporate a drill guide or fastener guide for one or more fasteners or reference pins. The pins may be placed into the pelvis, in or near the acetabulum, to provide a reference position to align an axis of an acetabular reamer and inserter in one or more planes. These planes aid, for example, in proper placement of an acetabular component in anteversion and inclination orientation. FIG. 5 illustrates an isometric view of the acetabulum 20. In the depicted embodiment, the CSFHAC 300 includes a drill guide 310. The drill guide 310 has one or more arms 320, each having a drill hole 330. The drill hole 330 is used to drill into or near the acetabulum 20 for placement of a reference pin (not shown) concentric with the drill hole 330. The drill hole 330 illustrated serves as a fastener guide and is configured to direct a bone fastener along a trajectory into the bone to establish and maintain a relative position of an acetabular component relative to the bone. Fastener guides of various embodiments may be of any effective shape or size and may or may not include one or more round holes for receiving fasteners. Any effective mechanism for guiding accompanying fasteners may be used. Offsets or other positioners may also be used.

Method embodiments of aligning an acetabular component based on a position of a femur relative to an acetabulum may include providing medical instruments similar to the medical instruments described with reference to FIGS. 1-5 herein, and other medical instruments that may be used to help carry out the methods described herein. Reference will be made additionally to FIGS. 6-17 to facilitate description of method embodiments. The medical instrument of FIGS. 6-13 is similar to the medical instrument of FIGS. 1-4, and the medical instrument of FIG. 5, but includes a single fastener guide. In particular, a CSFHAC 400 includes a drill guide 410 and an arm 420. The arm 420 includes a drill hole (not shown) that provides guidance for a drill or a fastener similar to the drill hole 330 illustrated in FIG. 5. Method embodiments of aligning an acetabular component based on a position of a femur relative to an acetabulum may also include coupling the medical instrument in a predetermined relationship with the femur. As illustrated in FIG. 6, the broach 100 of the medical instrument is fixed in the femur 30. The femoral coupling depicted is an intramedullary fixation, but in other embodiments, a femoral coupling may be by any other effective mechanism, including by extramedullary coupling. The example method embodiment also includes positioning the femur 30 in a first position relative to the acetabulum 20. As illustrated, the positioning of the femur in the first position may also include engaging the acetabular interface in the acetabulum 20. As shown in FIGS. 6-9, the first position of the femur 30 is a substantially neutral position, which may be referred to in the field as a "straight leg" position. As discussed herein, a neutral position includes positions near a neutral position. An inclination angle 445 of approximately 45 degrees is shown in FIG. 9 for the rim of the CSFHAC 400. The position of the rim of the CSFHAC 400 illustrated is analogous to a rim of an acetabular component or shell that may be implanted after alignment with the aid of the medical instrument. This is a typical inclination angle for a neutral leg positioning, but inclination angles may regularly fall within the range of about 40-50 degrees. As depicted in FIGS. 10 and 11, the femur 30 may remain in the neutral position relative to the acetabulum 20 while a tibia 40 is moved relative to the femur 30 to flex the knee. As shown in FIG. 10, the flexion of the knee is approximately 90 degrees. Flexion in the range of about 60-120 degrees may be accomplished in various embodiments. Flexion of the knee is not essential to all methods, but may be useful in some embodiments to provide a reference for additional steps of the methods. As illustrated in FIG. 11, the tibia 40, and more particularly a tibial axis 41, may be maintained parallel to an axis 3 on the floor as a reference for further rotation of the tibia 40.

Method embodiments may also include moving the femur 30 to a second position relative to the acetabulum 20. As illustrated in FIG. 12, moving the femur 30 from a first position in the direction of the arc 5 to a second position may include rotating the femur 30 in anteversion. The tibial axis 41 may be used as an estimation of degrees rotated in anteversion. In some embodiments, rotation in anteversion may include rotating the femur in a range of about 15-30 degrees. Some embodiments may include femoral rotation of about 25 degrees. Such a rotation may approach an extent of a typical range of motion of a femur in some patients.

Embodiments of methods also include recording the position of the acetabular interface relative to the acetabulum. Such recording may be accomplished by any effective technique, but two specific example techniques are illustrated in FIGS. 13-17. One example technique involves marking the acetabulum 20, as illustrated in FIG. 17. A CSFHAC 500 is shown in the acetabulum 20 following movement of the femur 30 to the second position. In the illustrated embodiment, a pen 21 is used to mark points 22 at which indicia 530 or, in some embodiments a rim of the CSFHAC 500 intersects edges of the acetabulum 20 when in the proper position. Other embodiments may use any effective marking device, such as, for example, a cauterizer. The indicia 530 may be parallel and spaced apart to provide a reference. In another example, indicia may include alphabetical characters or numeral characters. In some embodiments, there may be provided an acetabular shell or component with corresponding indicia to assist with alignment of the acetabular shell or component.

A second example technique for recording the position of the acetabular interface relative to the acetabulum, as shown in FIGS. 13-16, involves fixing a fastener 470 through a fastener guide on the medical instrument to bone in or near the acetabulum. As illustrated, the fastener 470 is fixed to the pelvis of the left hip 10 through a drill hole (not shown) in the arm 420 of the fastener guide. The fastener guide may be configured to allow the fastener 470 to be fixed essentially in parallel to an axis 700 defined by a center of the acetabulum. In some embodiments, the fastener guide may include guide holes that provide good surgical visibility and easy access.

Figure 18:
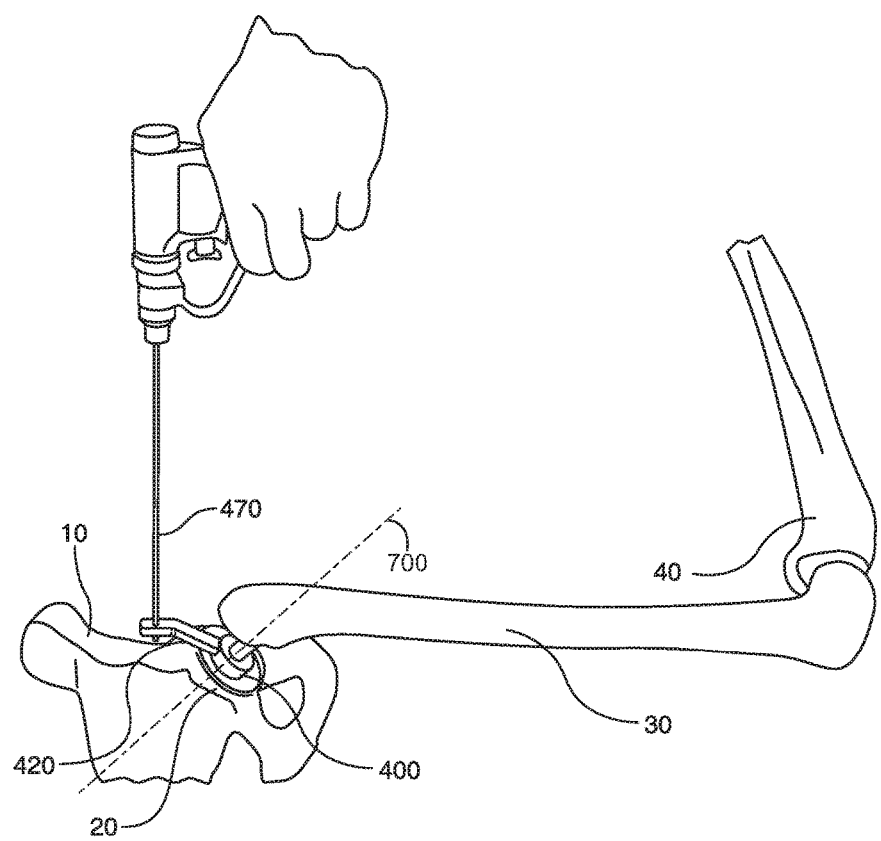
FIG. 18 illustrates a fastener attached to a pelvis along an axis that is not parallel to the axis of the native acetabulum.

In some implementations, a fastener guide on the medical instrument may guide a fastener into or near the acetabulum at an angle offset from the axis 700, as shown in FIG. 18, instead of parallel to the axis 700. In this embodiment, the arm 420 of the fastener guide includes a bend, such that the drill hole in the arm 420 guides a fastener 470 into the bone along an axis that is not parallel to the axis 700 of the acetabulum. This type of fastener guide may be preferred when insertion of a fastener is more easily achieved along directions different than the direction of the axis 700. For example, the surgical procedure and positioning of the patient may make visualization of the acetabulum along the axis 700 difficult. The arm 420 may be bent to present the drill hole along an axis, offset from axis 700, along which visualization is easier to achieve, for example from a posterior approach to the acetabulum. In certain implementations, a fastener guide may include multiple drill holes, with one or more aligned with the axis of the acetabulum and one or more others offset from that axis.

In some embodiments, an acetabulum may be reamed as part of the act of implanting an acetabular component based on the recorded position of the acetabular interface relative to the acetabulum. The act of reaming is illustrated in FIGS. 15 and 16. As shown in FIG. 14, before reaming or implanting of an acetabular component in a previously reamed acetabulum, the femur 30 may be dislocated and the CSFHAC 500 may be moved out of acetabulum, e.g., by sliding it out of the acetabulum in the direction of the free end of the fastener 470. A reamer 600 is illustrated in FIG. 15 engaged with and guided by the fastener 470. Therefore, implantation is guided by referencing the fastener 470. In other embodiments, more than one fastener 470, including fasteners fixed at different angles to an axis defined by a center of the acetabulum, or other types of fasteners as further discussed herein could be used to guide the implantation of an acetabular shell or other acetabula component.

The act of implanting the acetabular component based on the recorded position of the acetabular interface in the acetabulum may also be guided by visualizing one or more marks on the acetabulum. For instance, with reference to FIG. 17, the points 22 at which indicia 530 or a rim of the CSFHAC 500, or both, intersect the acetabulum 20 may be visualized and used to guide implantation or acts that are a part of implantation. Such techniques may be combined to provide alignment options intraoperatively or to improve overall accuracy of acetabular component placement. For example and without limitation, in FIG. 17 a fastener 470 as well as the points 22 could be used to guide implantation.

Based on the techniques described and other embodiments within the scope of the disclosure, acetabular components such as acetabular shells may be accurately and effectively implanted as described based on the recorded position of the acetabular interface in an acetabulum. The unique characteristics of the medical instruments described in detail herein enables the methods available within the scope of the disclosure made.

Another method to guide the surgeon is to utilize positional sensors to create planes of reference independent of anatomic landmarks but corresponding to the key locations or references that a surgeon currently utilizes for determination of proper cup placement; hence avoiding the registration issues of previous navigation systems and allowing the surgeon to utilize activities typically perform intraoperatively to create a reference environment for proper placement of the component. In other embodiments, a reference coordinate system on the pelvis to which the relationship of another coordinate system located on the femur or extension of the femur (e.g. neck or head—either native or part of the replacement) may be used.

Another technique may be to utilize positional type sensors. These sensors typically are capable of having their own coordinate systems. The sensors can relate positional and special orientation relative to each other or a predetermined coordinate system (e.g., one could establish a coordinate system based on the acetabulum center of rotation and anterior superior iliac spine, or ASIS). The concept of this embodiment is that a pair of sensors is incorporated into a unitized sensor element (USE) with a known relative location to each other and placed on the acetabulum one or more fasteners, such as a screw or pin. In one particular embodiment, the USE sensor is placed with two pins. Once placed a series of planes can be established based upon the location of the pelvic USE. Another USE is placed on the femur in relative alignment to the axis of the femur and on the proximal end. The hip is rotated so that the center of articulation is located by the relative motion of the femoral USE around a central point of rotation. The location center of the femoral head can then be determined from both the femoral and pelvic USEs. It is also possible that the following items could be determined: the neck axis, femoral axis, femoral offset, and a relative measurement of the leg length. If the leg is moved through the extremes of range of motion, a cone of motion can be created for the individual patient. The leg is then placed into a neutral position, a typical position in which the surgeon would characteristically assess the hip. Once in the neutral position, the coordinates of the position are identified and saved. This position provides insight into the inclination angle desired for the acetabular component placement. Next, the leg is positioned into combined internal rotation and flexion. This position may be saved. This position provides the information with regard to the anteversion of the acetabular component placement.

Having the information of the center of articulation, neck axis, relative location information regarding anteversion and inclination angle, and supplying additional information with regard to component design/option characteristics, the acetabular component position orientation may be estimated. If desired a sensor may be attached to the acetabular reamer handle to guide the reamer in the orientation determined previously so that the native acetabulum is prepared to receive the acetabular component in the correct orientation. Once the native acetabulum is reamed, a sensor is attached to the acetabular inserter to guide the path of the attached acetabular component into the native acetabulum with the previously determined anteversion and inclination angle orientation, (the surgeon would have the ability to set the desired amount of anteversion and inclination angle either on a per patient basis or as a general preference).

The placement of the femoral broach and implant also may be tracked if desired by placing sensors on the broach and stem inserter handles provides information of the femoral stem placement. With the placement of a femoral head and the reduction of the hip, the total version, femoral offset and leg length can all be determined.

Changes to the neck length of the femoral head may be tracked by either inputting the information directly or by the utilization of sensors. The same is true for the utilization of acetabular liners; sensors may be utilized to identify the type and orientation of the liner. The leg again may be moved into neutral and the combined internal rotation and flexion position and the cone of motion insure that the patient's range of motion and resistance to dislocation has been optimized if not liner and femoral head type and or orientation could be modified or changed based on the feedback provided.

A modification of this method is to place a USE on the pelvis to establish the fixed reference planes. The femur may be prepared in the normal manner prior to preparation of the acetabulum. The broach or a femoral implant is placed into the femur. A sensor is attached to the broach, implant, femur or both. A trial head is attached to the broach or the femoral implant. It is taken through a series of movements to locate the various positions and landmarks described previously. The trial head may or may not have mapping marks on the head. Again, as described previously the orientation of the acetabular component would be determined, and sensor would then be attached to the acetabular reamer and acetabular implant impactor to guide the implant into the pre-determined location and orientation.

In lieu of having to attach the sensor to the broach or implant, the sensor could be placed into the trial head. The trial head may be of a size to articulate in the native acetabulum to assist in the initial placement of the acetabular implant and/or to articulate in the artificial bearing component as a final check of proper component positioning.

If it is desired to reference the rim of the acetabulum, then a trial acetabular liner and sensor, of the appropriate size that would fit into the native or reamed acetabulum, may be inserted into the acetabulum. There also may be a lip or a series of protrusions that references the rim of the acetabulum such that an orientation axis through the center of the acetabulum would be determined with the sensor. The acetabular component placement may then be determined by any of the aforementioned methods and compared to the opening of the rim of the acetabulum; corrections to the implant position could be made if desired.

The uniqueness of some embodiments of the invention are the instruments and techniques useful in determining the proper orientation of the acetabular component initially based upon the femur. This allows for incorporation of the anteversion of the femur much earlier in the surgical technique than previous methods. There can be significant variation in patient femoral anteversion that is difficult, if not impossible, to address when assessing acetabular component placement from the pelvic side first. This possibly may contribute to the typically 4 to 6% post-operative dislocation rate in THA.

There is provided a medical instrument for aligning an acetabular component based upon a position of a femur relative to an acetabulum, the medical instrument comprising: a femoral interface configured to couple with the femur to align the medical instrument in a predetermined relationship with the femur; an acetabular interface configured to be moved within the acetabulum to indicate a position for placement of the acetabular component within the acetabulum; and a body coupled between the femoral interface and the acetabular interface, wherein the body orients the acetabular interface in a fixed relationship with the femoral interface; wherein the fixed relationship of the acetabular interface relative to the femoral interface is substantially the same as the relationship between the acetabular component and a femoral component where the femur that is configured to be coupled with the femoral component is in a position relative to the acetabulum that is near an extent of a typical range of motion of the femur.

In some embodiments, the femoral interface includes an intramedullary component to couple with a medullary canal of the femur. In some embodiments, the acetabular interface is at least in part spherical. In some embodiments, the acetabular interface is hemispherical. In some embodiments, the acetabular interface includes indicia that provide a reference for marking the acetabulum to receive an acetabular component. In some embodiments, the acetabular interface includes indicia that provide a reference for determining the size and orientation of the acetabular interface relative to the acetabulum. In some embodiments, the acetabular interface is configured to be moved within a reamed acetabulum. In some embodiments, the acetabular interface is configured to be moved within an unreamed acetabulum. In some embodiments, the femoral interface, the acetabular interface, and the body are a single piece. In some embodiments, the acetabular interface and the body are a single piece and the femoral interface is configured to removably affix to the body. In some embodiments, the femoral interface and the body are a single piece and the acetabular interface is configured to removably affix to the body. In some embodiments, when the femur coupled to the medical instrument is in the position relative to the acetabulum that is near the extent of a typical range of motion of the femur in the predetermined position, the position of the acetabular component in the acetabulum is a desired position. In some embodiments, the desired position of the acetabular component is a position where a plane of a rim of the acetabular component is substantially parallel with a periphery of the acetabulum. In some embodiments, when the femur is in a position relative to the acetabulum that is near the extent of a typical range of motion of the femur, the femur has been moved from a generally neutral position to a rotated position by rotating the femur in a range of about 15-30 degrees of anteversion. In some embodiments, when the femur is in a position relative to the acetabulum that is near the extent of a typical range of motion of the femur, the femur has been moved from a generally neutral position to a rotated position by rotating the femur by about 25 degrees of anteversion. In some embodiments, the medical instrument includes a fastener guide configured to direct a bone fastener along a trajectory into bone to establish and maintain a relative position for an acetabular component relative to the bone.

There is provided a medical instrument of a fixed, non-articulating shape that mimics the combined shape of a femoral hip replacement component designed to articulate with an acetabular hip replacement component, wherein the shape that is mimicked is the combined shape of the femoral hip replacement component and the acetabular hip replacement component when a femur that is configured to be coupled with the femoral component is in a position relative to the acetabulum that is near an extent of a typical range of motion of the femur.

In some embodiments, when the femur coupled to the medical instrument is in the position relative to the acetabulum that is near the extent of a typical range of motion of the femur, the position of the acetabular component in the acetabulum is a desired position. In some embodiments, the desired position of the medical instrument in the acetabulum is a position where a plane of a rim of an acetabular component of the medical instrument is substantially parallel with a periphery of the acetabulum. In some embodiments, when the femur is in a position relative to the acetabulum that is near the extent of a typical range of motion of the femur, the femur has been moved from a generally neutral position to a rotated position by rotating the femur in a range of about 15-30 degrees of anteversion. In some embodiments, when the femur is in a position relative to the acetabulum that is near the extent of a typical range of motion of the femur, the femur has been moved from a generally neutral position to a rotated position by rotating the femur by about 25 degrees of anteversion.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to medical devices to be used in other surgical procedures including, but not limited to, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

What is claimed is:

1. A method for aligning and implanting an acetabular component using a trial component, the method comprising:
    coupling the trial component to a femur to align the trial component in a fixed, predetermined relationship with the femur;
    placing the trial component into an acetabulum, wherein the trial component is configured to be moved within the acetabulum via the femur to indicate a position for implanting the acetabular component within the acetabulum;
    positioning the femur in a first position relative to the acetabulum;

moving the femur from the first position to a second position relative to the acetabulum, wherein the fixed relationship between the trial component and the femur causes the trial component to move relative to the acetabulum;

recording a position of the trial component relative to the acetabulum when the femur is in the second position; and implanting the acetabular component based on the recorded position of the trial component.

2. The method of claim 1, wherein recording a position of the trial component relative to the acetabulum comprises marking the acetabulum.

3. The method of claim 2, wherein a surface of the trial component facing the acetabulum comprises indicia, and wherein marking the acetabulum comprises marking locations on the acetabulum at which the indicia intersect edges of the acetabulum.

4. The method of claim 3, wherein a surface of the acetabular component facing the acetabulum comprises additional indicia, and wherein implanting the acetabular component based on the recorded position of the trial component further comprises aligning the additional indicia relative to the marked locations.

5. The method of claim 2, wherein marking the acetabulum comprises marking locations at which a rim of the trial component intersects edges of the acetabulum.

6. The method of claim 1, wherein recording a position of the trial component relative to the acetabulum comprises fixing a fastener into or near the acetabulum through a fastener guide formed in the trial component.

7. A trial medical instrument for aligning an acetabular component, comprising:
a first portion configured to fit within a patient's acetabulum; and
a second portion extending from the first portion;
wherein the second portion extends from the first portion in a direction that mimics a shape formed by a femoral implant component coupled with an acetabular implant component when a femur to which the femoral implant component is coupled is in a position relative to an acetabulum to which the acetabular implant component is coupled that is near an extent of a typical range of motion of the femur; and
indicia etched into a surface of the first portion that is configured to face the acetabulum, wherein the indicia are configured to provide a reference for alignment relative to the acetabulum.

8. The trial medical instrument of claim 7, comprising a fastener guide configured to direct a fastener along a trajectory into or near the acetabulum to mark a desired position of the first portion relative to the acetabulum.

9. A medical instrument for aligning an acetabular component based upon a position of a femur relative to an acetabulum, the medical instrument comprising:
a femoral interface configured to couple with the femur to align the medical instrument in a predetermined relationship with the femur;
an acetabular interface configured to be moved within the acetabulum to indicate a position for placement of the acetabular component within the acetabulum; and
a body coupled between the femoral interface and the acetabular interface, wherein the body orients the acetabular interface in a fixed relationship with the femoral interface; wherein the fixed relationship of the acetabular interface relative to the femoral interface is substantially the same as the relationship between the acetabular component and a femoral component where the femur that is configured to be coupled with the femoral component is in a position relative to the acetabulum that is near an extent of a typical range of motion of the femur;
wherein the femoral interface, the acetabular interface, and the body are a single piece.

10. The medical instrument of claim 9 wherein the femoral interface includes an intramedullary component to couple with a medullary canal of the femur.

11. The medical instrument of claim 9 wherein the acetabular interface is at least in part spherical.

12. The medical instrument of claim 9 wherein the acetabular interface includes indicia that provide a reference for marking the acetabulum to receive an acetabular component.

13. The medical instrument of claim 9 wherein the acetabular interface includes indicia that provide a reference for determining the size and orientation of the acetabular interface relative to the acetabulum.

14. The medical instrument of claim 9 wherein the acetabular interface is configured to be moved within a reamed acetabulum.

15. The medical instrument of claim 9 wherein the acetabular interface is configured to be moved within an unreamed acetabulum.

16. The medical instrument of claim 9 wherein when the femur coupled to the medical instrument is in the position relative to the acetabulum that is near the extent of a typical range of motion of the femur in the predetermined position, the position of the acetabular component in the acetabulum is a desired position.

17. The medical instrument of claim 9 wherein when the femur is in a position relative to the acetabulum that is near the extent of a typical range of motion of the femur, the femur has been moved from a generally neutral position to a rotated position by rotating the femur in a range of about 15-30 degrees of anteversion.

18. The medical instrument of claim 9 wherein the medical instrument includes a fastener guide configured to direct a bone fastener along a trajectory into bone to establish and maintain a relative position for an acetabular component relative to the bone.

19. A medical instrument of a fixed, non-articulating shape that mimics the combined shape of a femoral hip replacement component designed to articulate with an acetabular hip replacement component, wherein the shape that is mimicked is the combined shape of the femoral hip replacement component and the acetabular hip replacement component when a femur that is configured to be coupled with the femoral component is in a position relative to the acetabulum that is near an extent of a typical range of motion of the femur.

20. The medical instrument of claim 19 wherein when the femur coupled to the medical instrument is in the position relative to the acetabulum that is near the extent of a typical range of motion of the femur, the position of the acetabular component in the acetabulum is a desired position.

21. The medical instrument of claim 19 wherein when the femur is in a position relative to the acetabulum that is near the extent of a typical range of motion of the femur, the femur has been moved from a generally neutral position to a rotated position by rotating the femur in a range of about 15-30 degrees of anteversion.

22. A method of aligning an acetabular component based on a position of a femur relative to an acetabulum comprising:

providing a medical instrument for aligning the acetabular component comprising: a femoral interface configured to couple with the femur to align the medical instrument in a predetermined relationship with the femur, an acetabular interface configured to be moved within the acetabulum to indicate a position for placement of the acetabular component within the acetabulum, and a body coupled between the femoral interface and the acetabular interface, wherein the body orients the acetabular interface in a fixed relationship with the femoral interface;

coupling the medical instrument to the femur to align the medical instrument in a predetermined relationship with the femur;

positioning the femur in a first position relative to the acetabulum;

moving the femur to a second position relative to the acetabulum;

recording the position of the acetabular interface relative to the acetabulum; and implanting the acetabular component based on the recorded position of the acetabular interface relative to the acetabulum.

23. The method of claim 22 wherein the act of positioning the femur in a first position includes positioning the femur in a substantially neutral position.

24. The method of claim 22 wherein the act of moving the femur to a second position includes rotating the femur in anteversion.

25. The method of claim 24 wherein the act of rotating the femur in anteversion includes rotating the femur in a range of about 15-30 degrees.

26. The method of claim 22 further comprising, flexing a knee at the distal end of the femur after the act of positioning the femur in the first position.

27. The method of claim 22 wherein the act of recording the position of the acetabular interface relative to the acetabulum includes marking the acetabulum.

28. The method of claim 22 wherein the act of recording the position of the acetabular interface relative to the acetabulum includes fixing a fastener through a fastener guide on the medical instrument to bone in or near the acetabulum.

29. A medical instrument for aligning an acetabular component based upon a position of a femur relative to an acetabulum, the medical instrument comprising:

a femoral interface configured to couple with the femur to align the medical instrument in a predetermined relationship with the femur;

an acetabular interface configured to be moved within the acetabulum to indicate a position for placement of the acetabular component within the acetabulum; and a body coupled between the femoral interface and the acetabular interface, wherein the body orients the acetabular interface in a fixed relationship with the femoral interface; wherein the fixed relationship of the acetabular interface relative to the femoral interface is substantially the same as the relationship between the acetabular component and a femoral component where the femur that is configured to be coupled with the femoral component is in a position relative to the acetabulum that is near an extent of a typical range of motion of the femur;

wherein the acetabular interface and the body are a single piece and the femoral interface is configured to removably affix to the body.

30. A medical instrument for aligning an acetabular component based upon a position of a femur relative to an acetabulum, the medical instrument comprising:

a femoral interface configured to couple with the femur to align the medical instrument in a predetermined relationship with the femur;

an acetabular interface configured to be moved within the acetabulum to indicate a position for placement of the acetabular component within the acetabulum; and a body coupled between the femoral interface and the acetabular interface, wherein the body orients the acetabular interface in a fixed relationship with the femoral interface; wherein the fixed relationship of the acetabular interface relative to the femoral interface is substantially the same as the relationship between the acetabular component and a femoral component where the femur that is configured to be coupled with the femoral component is in a position relative to the acetabulum that is near an extent of a typical range of motion of the femur;

wherein the femoral interface and the body are a single piece and the acetabular interface is configured to removably affix to the body.

* * * * *